(12) United States Patent
Lee et al.

(10) Patent No.: US 7,198,626 B2
(45) Date of Patent: Apr. 3, 2007

(54) METHODS AND DEVICES FOR RADIOFREQUENCY ELECTROSURGERY

(75) Inventors: Roberta Lee, Redwood City, CA (US); Ary S. Chernomorsky, Millbrae, CA (US); Mark J. Clifford, Los Altos, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 0 days.

(21) Appl. No.: 10/349,659

(22) Filed: Jan. 23, 2003

(65) Prior Publication Data

US 2003/0109870 A1 Jun. 12, 2003

Related U.S. Application Data

(62) Division of application No. 09/732,848, filed on Dec. 7, 2000, now abandoned.

(51) Int. Cl.
*A61B 18/18* (2006.01)
*A61B 17/24* (2006.01)

(52) U.S. Cl. .................... 606/47; 606/114

(58) Field of Classification Search ........ 606/113, 606/127, 37–41, 45–50, 114; 607/101, 102
See application file for complete search history.

(56) References Cited

U.S. PATENT DOCUMENTS

| | | |
|---|---|---|
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada |
| 4,245,653 A | 1/1981 | Weaver |

(Continued)

FOREIGN PATENT DOCUMENTS

DE 195 28 440 A1 2/1997

(Continued)

OTHER PUBLICATIONS

Ulmer et al, *Electrosurgery Self-Study Guide*, Sep. 1997.

(Continued)

*Primary Examiner*—Michael Peffley
(74) *Attorney, Agent, or Firm*—Young Law Firm, P.C.

(57) ABSTRACT

An electrically activated surgical device includes a probe body, an active element and a structure for selectively electrically insulating and/or physically isolating the active element from the patient's tissue when the device is in use. The probe body defines an outer surface, a proximal end, a distal end and a window defined within the outer surface near or at the distal end. The active element is electrically connected to a power source and is configured to selectively assume a non-deployed configuration and a variable deployed configuration in which the active element at least partially emerges from the window out of the probe body. The insulating structure selectively insulates the active element from the patient's tissue when the device is inserted therein. In operation, a physician inserts the probe into the tissue, insulates the active element from the tissue (either before, during or after insertion of the probe), energizes the insulated active element using for example, radiofrequency (RF) power from the power source, and only then exposes the energized active element to the tissue. By insulating the active element during the energizing thereof, little or no current applied to the active element is dissipated in the patient's tissue, thus decreasing the time required to energize the active element and enabling lower and safer power levels to be applied to the active element during the energizing thereof.

9 Claims, 9 Drawing Sheets

U.S. PATENT DOCUMENTS

| | | |
|---|---|---|
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh |
| 5,156,610 A | 10/1992 | Reger |
| 5,174,296 A | 12/1992 | Watanabe |
| 5,176,688 A | 1/1993 | Narayan |
| 5,192,291 A | 3/1993 | Pannek |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek |
| 5,282,484 A | 2/1994 | Reger |
| 5,308,321 A | 5/1994 | Castro |
| 5,318,576 A | 6/1994 | Plassche |
| 5,325,860 A | 7/1994 | Seward |
| 5,403,311 A * | 4/1995 | Abele et al. .................. 606/49 |
| 5,415,656 A | 5/1995 | Tihon et al. |
| 5,441,510 A | 8/1995 | Simpson |
| 5,458,597 A * | 10/1995 | Edwards et al. .............. 606/41 |
| 5,527,326 A | 6/1996 | Hermann |
| 5,554,163 A | 9/1996 | Shturman |
| 5,630,426 A | 5/1997 | Eggers |
| 5,632,754 A | 5/1997 | Farley |
| 5,672,172 A | 9/1997 | Zupkas |
| 5,683,384 A * | 11/1997 | Gough et al. ................. 606/41 |
| 5,709,697 A | 1/1998 | Ratcliff |
| 5,741,271 A | 4/1998 | Nakao et al. |
| 5,766,191 A | 6/1998 | Trerotola |
| 5,794,626 A | 8/1998 | Kieturakis |
| 5,797,907 A * | 8/1998 | Clement ...................... 606/49 |
| 5,800,484 A * | 9/1998 | Gough et al. ............... 607/104 |
| 5,810,806 A * | 9/1998 | Ritchart et al. ............... 606/45 |
| 5,895,399 A | 4/1999 | Barbut |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Sciver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,179,860 B1 | 1/2001 | Fulton, III et al. |
| 6,200,313 B1 | 3/2001 | Abe et al. |
| 6,221,006 B1 | 4/2001 | Dubrul et al. |
| 6,238,389 B1 | 5/2001 | Paddock et al. |
| 6,287,304 B1 * | 9/2001 | Eggers et al. .................. 606/37 |
| 6,325,797 B1 | 12/2001 | Stewart et al. |
| 6,331,166 B1 * | 12/2001 | Burbank et al. ............ 600/567 |

FOREIGN PATENT DOCUMENTS

| | | |
|---|---|---|
| DE | 197 06 751 A1 | 10/1997 |
| EP | 0 983 749 A2 | 3/2000 |
| GB | 2 204 496 A | 11/1988 |
| GB | 2311468 | 10/1997 |
| JP | 54-86991 | 10/1979 |
| JP | 10-99342 | 4/1998 |
| JP | 2000-116657 | 2/1999 |
| NZ | 202965 | 5/1985 |
| WO | WO 95/02370 | 1/1995 |
| WO | WO 95/02371 | 1/1995 |
| WO | WO 99/01074 | 1/1999 |
| WO | WO 99/44506 | 9/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

OTHER PUBLICATIONS

Radio Therapeutics, *Patient Information About Readiofrequency Ablation*, http://www.radiotherapeutics.com/patients/shtml.

Valleylab, *Educational Booklet on Electrosurgery*, http://www.valleylab.com.

Examiner's Report dated May 9, 2005, In related Australian Patent Application No. 2002225886.

Examination Report dated Apr. 26, 2005, in related New Zealand Patent Application No. 526314.

Office Action mailed Aug. 3, 2005, in related Japanese National Phase Application No. 2002-547396.

* cited by examiner

FIG. 39 even if the RF electrode were in contact with comparatively less vascularized tissue. Alternatively, the initial power applied to the RF electrode may need to be momentarily increased to achieve the same tissue effect in a fixed period of time.

METHODS AND DEVICES FOR RADIOFREQUENCY ELECTROSURGERY

CROSS-REFERENCE TO RELATED APPLICATIONS

The present application is a divisional of U.S. Ser. No. 09/732,848 filed Dec. 7, 2000 (now abandoned).

BACKGROUND OF THE INVENTION

1. Field of the Invention

The present invention relates primarily to the field of electrosurgery. In particular, the present invention relates to the field of radiofrequency (RF) electrosurgery, including RF cautery, RF dissection, RF fulguration or coagulation, RF desiccation or any other forms of RF-assisted electrosurgery.

2. Description of the Related Art

Electrosurgery generally refers to the use of electrically energized surgical devices to operate upon a patient. Common electrosurgical devices include electrocautery devices in which a direct current (DC) is caused to flow through a wire loop. The resistance of the wire causes the loop to heat up, thereby enabling the cauterization of the tissue.

More commonly, electrosurgical devices (whether monopolar or bipolar) utilize alternating current (AC) in the range of about 200 kHz to about 3.3 MHz (hereafter "RF") that is applied to the patient via a RF electrode. Such RF electrosurgical instruments are typically used to dissect (cut), fulgurate (coagulate) or desiccate (dry out) tissue by selectively varying the power and duty cycle of the RF signal applied to the electrode of the electrosurgical instrument. When the RF electrosurgical instrument is monopolar, a large low impedance return (dispersive) electrode is affixed to the patient to provide the current return path to ground. A bipolar RF electrosurgical instrument has two electrodes, the active electrode and the return electrode. The flow of current occurs between these two electrodes, thus obviating the need for a large low impedance return electrode. An insulated RF generator is typically used to energize the RF electrode(s) of the RF electrosurgical instrument.

The density of the current delivered to the active electrode may be affected by the impedance (a vector quantity consisting of the tissue's resistance and its reactance) of the tissue. The impedance of the tissue to which the electrodes are exposed has an important effect upon the functioning of RF electrosurgical devices. This is because the tissue becomes an integral part of the circuit comprising the RF generator, the active electrode, the patient's tissue, the return electrode and back to the RF generator to ground or a reference voltage. Therefore, a voltage controlled or limited RF generator (generally providing power between about 10 W and 200 W) is generally used, so that when the impedance of tissue rises, the current delivered to the active electrode safely decreases. The density and impedance of tissue affects the manner in which it is affected by the active electrode. Tissues with higher salt content and body fluids such as blood have a high conductance and therefore, lower impedance. Fatty tissues have a lower fluid content and generally exhibit relatively higher impedance than leaner tissues. Thus, for a given voltage, fatty tissue will dissipate less current than leaner tissue. Highly vascularized tissues, on the other hand, have very low impedance and tend to conduct current more efficiently than less vascularized tissues. Therefore, to achieve the same tissue effect, current must be applied to a RF electrode in contact with highly vascularized tissue for a longer period of time than would be the case if the RF electrode were in contact with comparatively less vascularized tissue. Alternatively, the initial power applied to the RF electrode may need to be momentarily increased to achieve the same tissue effect in a fixed period of time.

Figure 1:
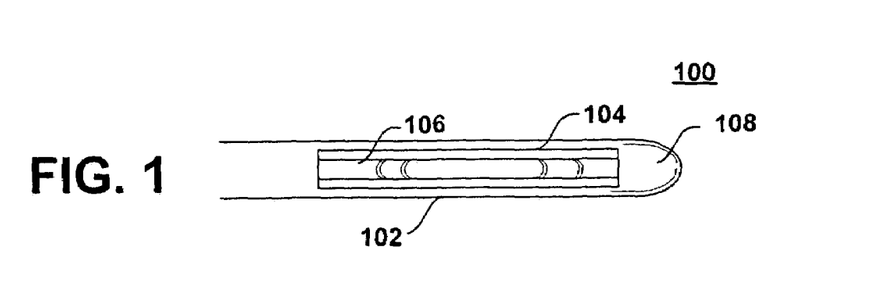
FIG. 1 is a top view of the distal end of an expandable loop excisional device.
Figure 2:
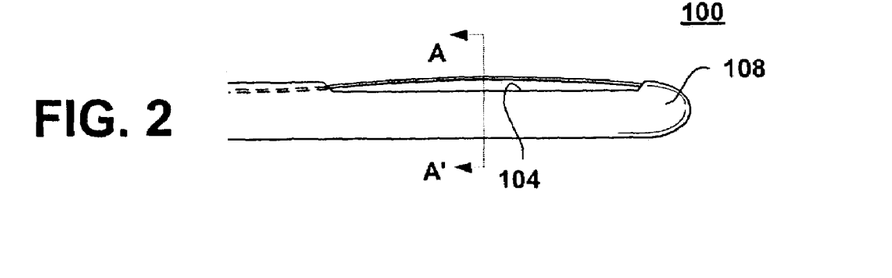
FIG. 2 is a side view of the distal end of the excisional device of FIG. 1, in which the loop is in its non-extended (non-deployed) configuration.
Figure 3:
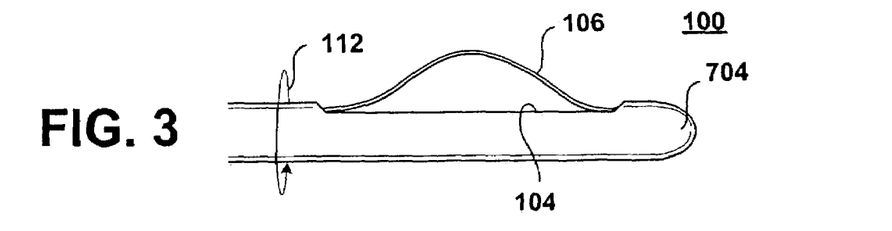
FIG. 3 is a side view of the distal end of the excisional device of FIG. 1, in which the loop is in its extended (deployed) configuration.
Figure 4:
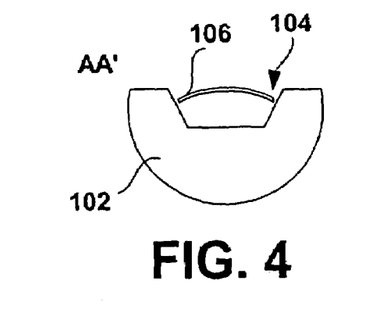
FIG. 4 is a cross-sectional view of the excisional device of FIG. 2, taken along cross-sectional lines AA'.

FIGS. 1–3 show a RF excisional device 100 that includes a probe 102, the distal end 108 of which includes a conductive ribbon or wire loop 106 configured to bow out of and back into a window 104 defined within the probe 102. The loop 106 is connected to a RF power supply (not shown). The loop 106 is energized with RF energy and the probe 102 is rotated as shown at 112 with the loop 106 in an extended or deployed configuration, as shown in FIG. 3. As the probe 102 is rotated, a volume of revolution of tissue is cut by the RF-energized loop 106.

However, when the loop 106 is in contact with the tissue to be cut, the physician often must wait a relatively long period of time (several seconds or longer) between initial application of the RF power to the loop 106 and the time at which the current density within the loop 106 is high enough to cut (vaporize) the tissue. This is because the relatively low impedance of the interface between the loop 106 and the patient's tissue shown at 114 in FIG. 5 dissipates a substantial amount of the current delivered to the loop 106. Highly vascularized tissue may also increase the current conduction (symbolized by the arrows emanating from the loop 106 in FIG. 5) away from the loop 106 and further delay the time at which the RF loop 106 is able to cut through the tissue 114. Indeed, until the tissue 114 chars and the impedance thereof increases, the current density within the loop 106 may not quickly reach that level at which the energized loop 106 is therapeutically effective.

Figure 5:
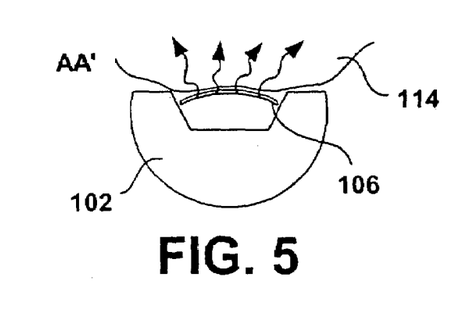
FIG. 5 shows the excisional device of FIG. 4 in which the loop is in contact with tissue, to illustrate the current dissipation occurring at the loop-tissue interface.
Figure 6:
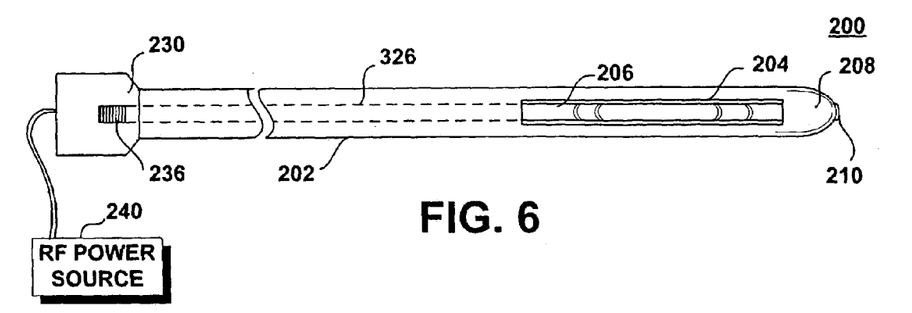
FIG. 6 shows an embodiment of a RF electrosurgical device, according to an embodiment of the present invention.
Figure 7:
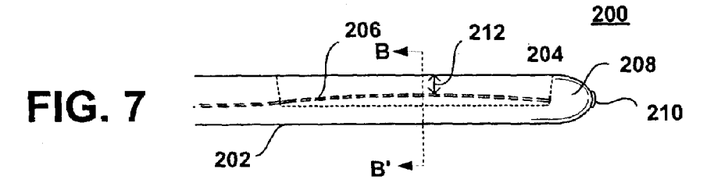
FIG. 7 shows the distal end of the RF electrosurgical device of FIG. 6, in which the active element thereof is in its non-extended (non-deployed) configuration.

One solution to this problem is to initially increase or surge the power delivered to the loop 106 to decrease the time required for the current density therein to reach the desired level. However, this is a less than optimal solution, as such an initial power surge may cause pain, excessive charring of the tissue 114 at the initial cut site, and may present a safety risk to the patient, who is better served by maintaining power levels as low as practicable to achieve the objective of the procedure. Such initial power surges, moreover, require specialized RF generators that are configured to deliver such surges safely and on demand.

What are needed, therefore, are improved methods and RF electrosurgical devices that do not suffer from the aforementioned disadvantages. More particularly, what are needed are RF electrosurgical devices that energize quickly, cut more efficiently and less painfully, reduce tissue charring at the initial cut site, and do not require an initial power surge from a specialized RF generator.

SUMMARY OF THE INVENTION

It is, therefore, an object of the present invention to provide methods and RF electrosurgical instruments that do not suffer from the aforementioned disadvantages. It is also an object of the present invention to provide RF electrosurgical instruments that energize quickly, are safer, cut more efficiently and less painfully, reduce tissue charring at the initial cut site and do not require an initial power surge from a specialized RF generator.

In accordance with the above-described objects and those that will be mentioned and will become apparent below, an electrosurgical device according to an embodiment of the present invention, includes a body, the body defining an outer surface, a proximal end, a distal end and a window defined within the outer surface; an electrically insulating layer and an active element, the active element being adapted to electrically connect to a power source and configured to selectively assume a non-deployed configuration in which the insulating layer electrically insulates the active element from a patient's tissue when the device is in use and a variable deployed configuration in which the active element at least partially emerges from the window out of the body to make contact with the patient's tissue.

The active element may include one of a ribbon and wire, said one of ribbon and wire being adapted to selectively bow out of the window when transitioning from the non-deployed configuration to the deployed configuration. A tissue collection means may be attached thereto or trail behind the active element, as shown at 302 in FIG. 30 and as disclosed in co-pending and commonly assigned U.S. patent application Ser. No. 09/565,611 filed on May 4, 2000 and/or commonly assigned U.S. Pat. No. 6,022,362 filed on Sep. 3, 1998, the disclosure of each being incorporated herein by reference in its entirety.

The active element may be configured to carry tissue ablation, dissection, fulguration, cautery, desiccation, hyperthermia or hypothermia, for example. The thickness of the insulating layer may be selected within a range of about 0.1 mm to about 5 mm, for example. The power source may include a RF power source. The window may be disposed near the distal end of the body or at the distal end thereof. The active element may be ring-shaped and may include a trailing tissue collection means attached thereto adapted to collect tissue cut by the ring-shaped active element. The insulating layer may include an electrically insulating sliding door mounted within the body, the sliding door being configured to selectively cover at least a portion of the window. The sliding door may be configured to slide between a variable first position in which at least a portion of the active element is exposed to the patient's tissue through the window and a second position in which the sliding door electrically insulates the active element within the body from the patient's tissue. The insulating layer may include a layer of air and the window may be configured to maintain the layer in the non-deployed configuration. The insulating layer may include an electrically insulating outer sleeve configured to selectively slide over the outer surface of the body, the outer sleeve being configured to at least partially cover the active element to electrically insulate the active element from the patient's tissue and uncover the active element to expose the active element to the patient's tissue. The insulating layer further may include an electrically insulating sheath disposed around at least a portion of the device body, the insulating sheath defining a cutaway portion aligned with the window and defining one or more raised portions configured to prevent the patient's tissue from prolapsing into the window when the active element is in its non-deployed configuration. The insulating layer may include an insulating sleeve disposed at least partially around the active element, the insulating sleeve being configured to controllably slide over the active element to selectively electrically insulate the active element from the patient's tissue and expose the active element thereto when the device is in use. The body may be shaped as a non-coring needle. The insulating layer may include a layer of air and the device body may define one or more raised portions adjacent the window, the raised portion(s) maintaining the layer of air between the active element and the patient's tissue when the active element is in its non-deployed state. Suction means may be included within the body for controllably removing fluids from the operative site within the patient's tissue.

The present invention may also be viewed as a method of treating tissue using a probe, the probe including an active element that may be extendable out of and retractable back into a window defined in the probe, the active element being electrically connected to a power source, comprising the steps of: inserting the probe into the tissue; electrically insulating the active element from the tissue; energizing the active element using power from the power source, and exposing the energized active element to the tissue.

The power source may be adapted to supply RF power to the active element. The insulating step may include a step of maintaining an electrically insulating layer between the active element and the tissue. The probe further may include an electrically insulating sliding door and the insulating step may include a step of sliding the door across the window. The method may further comprise the step of inducing hyperthermia or hypothermia and necrosis in the tissue exposed to the active element. The probe further may include an electrically insulating outer sleeve adapted to slide over an outer surface of the probe and the insulating step may include a step of sliding the outer sleeve over the window. The probe further may include an insulating sheath around at least a portion of the probe body, the insulating sheath including at least one raised portion adjacent the window and the insulating step may include a step of maintaining the active element retracted within the window. The insulating step may include a step of maintaining the active element retracted within the window. The probe further may include an insulating sleeve adapted to slide over the active element and the insulating step may include a step of sliding the insulating sleeve over the active element. The insulating step may include a step of creating or maintaining a layer of air between the active element and the tissue. The probe further may include an inflatable balloon disposed adjacent the window, and the insulating step further may include a step of inflating the balloon to create a layer of air between the tissue and the active element.

The present invention is also an electrosurgical device, comprising a device body, the body defining a proximal end and a distal end; an active element coupled to the body, the active element being adapted to be controllably energized from a power source; and means for selectively electrically insulating and exposing the active element from and to a patient's tissue when the device is in use.

The active element may be configured to selectively assume a non-deployed configuration in which the active element is recessed within the body and a variable deployed configuration in which the active element at least partially emerges from the body. The active element may be configured to carry out tissue ablation, dissection, fulguration, cautery, desiccation, hyperthermia and/or hypothermia, for example. The active element may be configured to be energized by a RF power source, for example. The device body may define a window disposed near the distal end of the body, and the active element may be configured to selectively retract into and extend from the window. A window may be defined within the body and the insulating means may include an electrically insulating sliding door mounted within the body, the sliding door being configured to selectively cover at least a portion of the window. The sliding door may be configured to slide between a variable first position in which at least a portion of the active element is exposed through the window and a second position in which the sliding door electrically insulates the active element from the patient's tissue. The insulating means may be integral with the window and the window may be configured to prevent tissue from prolapsing therein and making physical and/or electrical contact with the active element when the active element is in a non-deployed configuration. The insulating means may include an electrically insulating outer sleeve configured to selectively slide over the outer surface of the body, the outer sleeve being configured to at least partially cover the active element and electrically insulate the active element from the patient's tissue when the device is in use and the active element is in a non-deployed configuration. The insulating means may include an electrically insulating sleeve disposed at least partially around the active element, the insulating sleeve being configured to controllably slide over the active element to selectively electrically insulate the active element from the patient's tissue and expose the active element thereto when the device is in use. The insulating means may be integral with the body and may define one or more raised portions, the raised portion(s) being configured to prevent tissue from making physical and/or electrical contact with the active element until the active element is deployed. The insulating means may include an electrically insulating sheath disposed over the body, the insulating sheath defining at least one raised portion configured to prevent the patient's tissue from coming into contact with the active element until the active element is deployed. The active element may be shaped as a ring and the insulating means may be integral with the distal end of the body, the ring-shaped active element being configured to be recessed away from the distal end of the body until fully energized.

The present invention is also an electrosurgical device adapted for insertion into tissue, comprising: a device body; a RF energizable active element disposed within the device body, and an insulating structure. The device body and/or the insulating structure may be configured to insulate the active element from the tissue until the active element is sufficiently energized to be therapeutically effective when the active element is brought into contact with the tissue.

DESCRIPTION OF THE INVENTION

Figure 8:
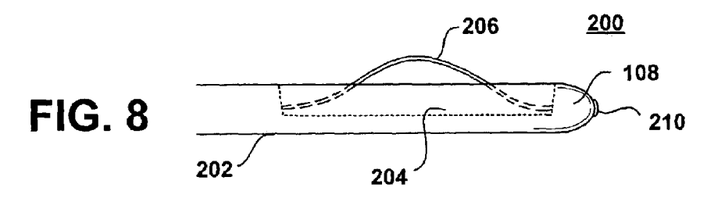
FIG. 8 shows the distal end of the RF electrosurgical device of FIG. 7, in which the active element thereof is in its extended (deployed) configuration.

FIGS. 6–10 show an embodiment of a RF electrosurgical device 200, according to the present invention. As shown therein, the device 200 includes a probe body 202, the probe body 202 defining an outer surface, a proximal end 230, a distal end 208 and a window 204 (shown in dashed lines in FIGS. 7 and 8) defined within the outer surface near the distal end 208. The probe 200 includes an active element 206. The active element 206 may include, for example one or more wires and/or loops, or any other therapeutically effective RF element effective to cut, dissect, fulgurate and/or desiccate tissue (for example) using RF power. The active element 206 may be electrically connected to a power source, such as the RF power source 240. A distal RF element 210 may also be mounted to the distal end 208 of the probe body 202, to facilitate penetration of the probe 200 into the patient's tissue. The distal RF element 210 may also be independently electrically connected to the RF power source 240. According to the present invention, the active element 206 may be configured to selectively assume a non-deployed configuration (FIG. 7) and a variable deployed configuration (FIG. 8). In the variable deployed configuration (FIG. 8), the active element 206 at least partially emerges from the window 204 out of the probe body 202. The deployment of the active element 206 may be controlled by the physician by means of an actuator 236, such as the thumb wheel shown in FIG. 6 or other actuation means. By turning the actuator 236 with his or her thumb, the physician causes the active element 206 to slide within a guide 326 defined within the probe 202. As the distal end of the active element 206 is attached to the distal end 208 of the probe 200, the active element 206 bows out of the window 204, the degree of bowing and deployment out of the window 204 being controlled by the actuator 236.

Figure 9:
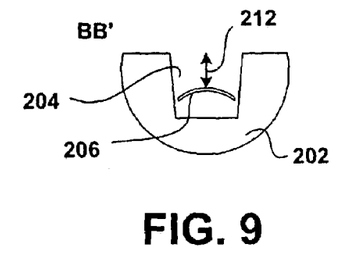
FIG. 9 is a cross-sectional view of the excisional device of FIG. 7, taken along cross-sectional lines BB'.
Figure 10:
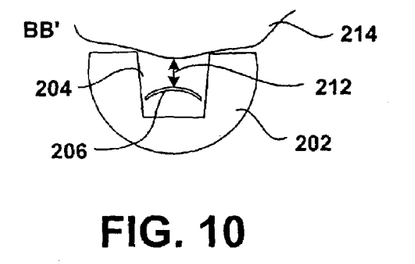
FIG. 10 shows the excisional device of FIG. 9 and illustrates the absence of active element-tissue interface when the RF electrosurgical device of the present invention is initially inserted in tissue and RF power applied to the active element.
Figure 11:
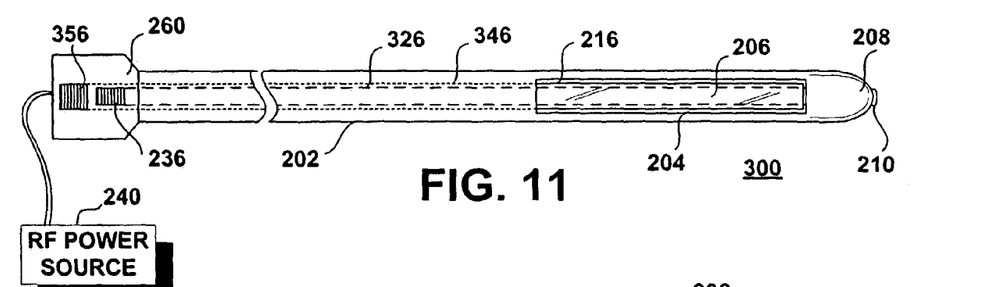
FIG. 11 shows another embodiment of a RF electrosurgical device, according to the present invention.
Figure 12:
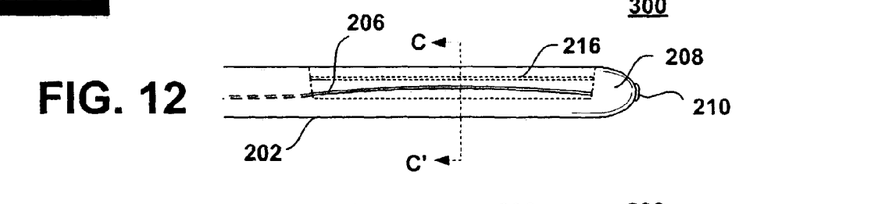
FIG. 12 shows the distal end of the RF electrosurgical device of FIG. 11, in which the active element thereof is in a non-extended (non-deployed configuration).
Figure 13A:
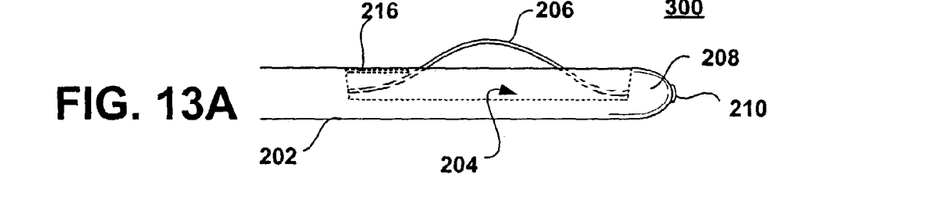
FIG. 13A shows the distal end of the RF electrosurgical device of FIG. 11, in which the active element thereof is in a first illustrative extended (deployed configuration).
Figure 13B:
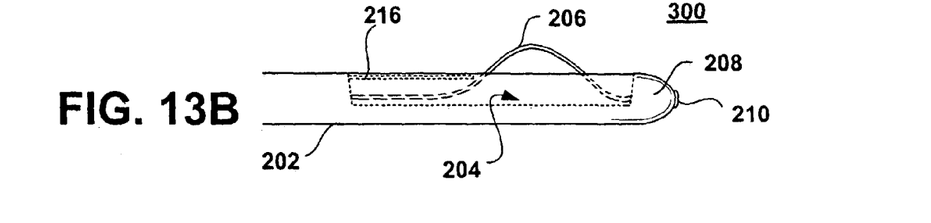
FIG. 13B shows the distal end of the RF electrosurgical device of FIG. 11, in which the active element thereof is in a second illustrative extended (deployed configuration).

In the non-deployed configuration, the active element 206 is recessed within the probe body 202 to define an insulating layer 212 (a layer of air, for example) with respect to the outer surface of the probe body 202. The recessed active element 206 and/or the presence of the insulating layer 212 enables the active element 206 to be energized without contacting the patient's tissue. Indeed, by avoiding contact with the patient's tissue during the energizing of the active element 206, the current delivered to the active element 206 is not dissipated by the patient's tissue that would otherwise be in contact therewith but for the presence of the insulating layer 212. According to the present invention, after the active element 206 is energized, the active element 206 may be deployed to (for example) cut, ablate or coagulate (depending upon the application) the patient's tissue without the physician having to wait for the tissue impedance to rise sufficiently (while the patient's tissue heats up and/or chars) to enable the current density within the active element 206 to reach the desired level for the procedure to be carried out. FIGS. 9 and 10 show a cross-sectional view of the probe 200, taken along the cross-sectional lines BB' of FIG. 7. As shown therein, to electrically insulate the active element 206 from the patient's tissue (reference 214 in FIG. 10), the window 204 defined within the probe body 202 may be shaped and/or dimensioned so as to prevent the tissue 214 through which the probe 200 is inserted from prolapsing therein. As shown, the window 204 is configured to define an electrically insulating layer 212 between the active element 206 and the patient's tissue 214 when the active element 206 is in its non-deployed (retracted) configuration. Toward that end, the window 204 may define a steep aspect ratio, in which the depth of the window 204 is greater than its width.

Figures 14, 15:
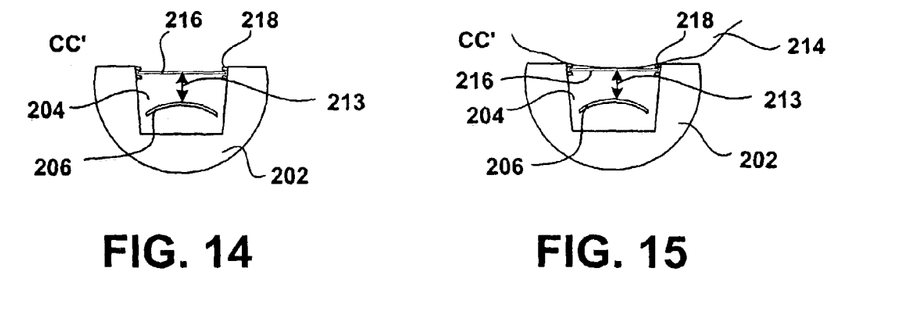
FIG. 14 is a cross-sectional view of the excisional device of FIG. 12, taken along cross-sectional lines CC'.
FIG. 15 shows the excisional device of FIG. 14 and illustrates the absence of active element-tissue interface when the RF electrosurgical device of the present invention is initially inserted in tissue and RF power is applied to the active element.

FIGS. 11–15 show a probe 300 according to another embodiment of the present invention. Reference numerals that are identical to those shown in FIGS. 6–10 denote identical structures. For the sake of brevity, the description of those identical structures will not be explicitly repeated here. In FIGS. 11–15, the insulating layer that electrically insulates the active element 206 from the patient's tissue 214 includes a sliding door 216 disposed within the probe body 202. The sliding door 216 may be made of an electrical insulator or other substantially non-conductive material or materials. The sliding door 216 is configured to selectively cover at least a portion of the window 204 to electrically insulate the active element 206 of the device 300 from the patient's tissue 214 until the active element 206 is fully energized and/or until the physician chooses to expose the active element 206 to the patient's tissue 214. The physician, according to the present invention, may cause the sliding door 216 to slide and expose the active element 206 by means of a sliding door actuator such as a manual thumb wheel, as shown at 356. It is understood that other means of acting upon the sliding door 216 and/or active element 206 may be employed, as the present invention is not limited to thumb wheel actuators, as shown at 356 and 236. According to the present invention, the sliding door 216 is configured to slide between a variable first position in which at least a portion of the active element is exposed through the window (as shown in FIGS. 13A and 13B) and a second position (shown in FIGS. 11, 12, 14 and 15) in which the sliding door 216 insulates the active element 206 within the probe body 202. As shown in FIGS. 13A and 13B, the sliding door 216 may be caused to expose a selectable portion of the active element 206 to the patient's tissue 214. In so doing, the sliding door 216 may affect the shape of the deployed active element: if the sliding door 216 is fully or near fully retracted as shown in FIG. 13A, a greater portion of the active element 206 may emerge from the window 204 than is the case wherein the sliding door 216 is only partially retracted and only exposes a portion of the window 204, as shown in FIG. 13B. This may enable the physician to control the extent of deployment and the shape of the extended active element 206. FIGS. 14 and 15 show the sliding door 216 as it covers the window 204, thereby electrically insulating the active element 206 from the patient's tissue 214. The sliding door 216 may be guided within the probe body 202 by means of, for example, internal guides or rails 218. Using this configuration, the physician may apply RF power to the active element 206 and begin the intended RF procedure (cutting, ablating, coagulating, etc.) sooner than would otherwise be the case if the de-energized active element were energized while in contact with the patient's tissue 214. The layer of air 213 between the active element 206 and the sliding door 216 may be reduced or eliminated altogether, as the sliding door 216 electrically insulates and physically isolates the active element 206 from the patient's tissue 214. The sliding door 216, for that purpose, is preferably formed of non-conductive material, such as a non-conductive plastic or ceramic, for example.

Figures 16, 17:
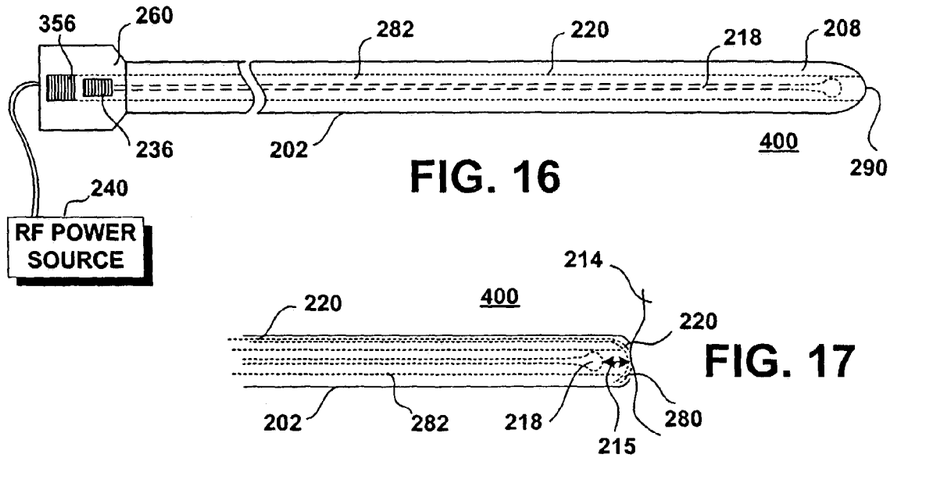
FIG. 16 is a top view of another embodiment of an electrosurgical device according to the present invention.
FIG. 17 shows a side view of the distal end of the electrosurgical device of FIG. 16, in which the active element thereof is in its non-deployed configuration.
Figure 18:
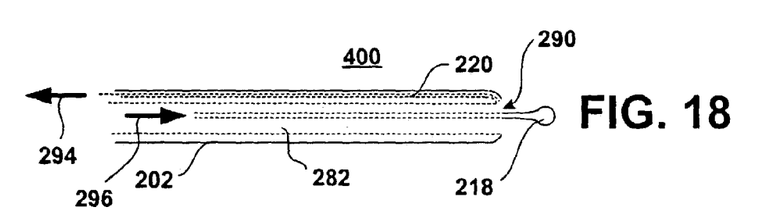
FIG. 18 shows the electrosurgical device of FIG. 17, in which the active element thereof is in its deployed configuration.

FIGS. 16–18 show another embodiment of the present invention. As shown therein, the electrosurgical device 400 includes a proximal end 260, a distal end 208, a probe body 202, an active element actuator 236 and a sliding door actuator 356, as described above. The distal tip of the probe body defines an opening 290 that is aligned with an internal lumen 282 defined within the probe body 202. The exemplary active element 218 shown in FIGS. 16–18 includes an elongated conductive stem that is distally terminated by a conductive bulb. However, any electrically active element may be used in conjunction with or in place of the active element depicted in FIGS. 16–18. The active element 218 may be electrically coupled to the RF power source 240. The bulb may be used, for example, to induce hyperthermia and/or necrosis in the tissue 214 with which it comes into contact. In that case, the duty cycle of the RF current applied to the active element 218 may be adjusted to be, for example, 50%–25%, so as to induce substantial heating in the tissue 214 in contact with the active element 218. In this embodiment, the insulating layer separating the active element 218 from the patient's tissue 214 when the active element 206 is in its non-deployed configuration may include a sliding and electrically insulating door 220 mounted within the probe body 202. The sliding door 220 may be configured to slide axially in the distal and proximal directions (away from and toward the physician, respectively, when the device 400 is in use) when the sliding door actuator 356 is actuated. The distal end of the sliding door 220 may be advantageously configured to cover (see FIG. 17) the opening 290 during insertion of the device 400 into the patient's tissue 214 and during the energizing of the active element 218. After the device 400 has been inserted up to the targeted site within the patient's tissue 214 and the active element 218 has been energized, the physician may actuate the sliding door actuator 356 to retract the sliding door 220 away from the opening 290, in the proximal direction 294. Thereafter, the energized active element 218 may be advanced in the distal direction 296 into the target area of the patient's tissue 214 to begin treatment thereof, as shown in FIG. 18. Alternatively, the sliding door 220 may be retracted before the active element 218 is energized. Thereafter, the active element 218 may be energized without dissipating current into the surrounding tissue 214, as the active element 218 is still recessed and electrically insulated from the patient's tissue by an air layer 215. The shape and/or size of the opening 290 and/or the thickness of the air layer 215 may also prevent the patient's tissue 214 from prolapsing into the opening 290, thereby further insulating the active element 218. As shown in FIGS. 16 and 17, the active element 218 is fully insulated from the patient's tissue 214 by the sliding door 220 until the active element 218 is appropriately energized, thereby preventing any disadvantageous dissipation of RF current into the tissue 214 upon the application of RF current to the active element 218.

Figure 19:
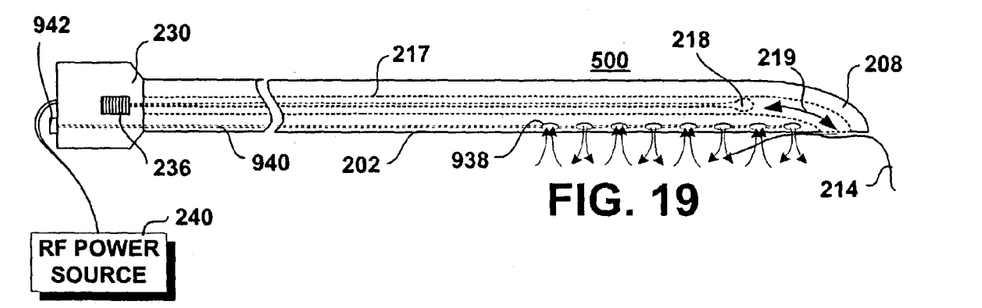
FIG. 19 shows a side view of another embodiment of an electrosurgical device according to the present invention, in which the active element thereof is in its non-deployed configuration.
Figure 20:
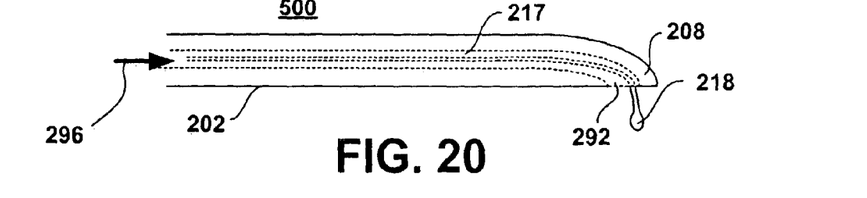
FIG. 20 shows the electrosurgical device of FIG. 19, in which the active element thereof is in its deployed configuration.

FIGS. 19–20 show a still further embodiment of the present invention. As shown therein, the electrosurgical device 500 includes a probe body 202 defining a proximal end 230, a distal end 208 and an internal lumen 217. The proximal end 230 includes an active element actuator 236, as described above. An active element 218 is configured to slide within the internal lumen 217, as controlled by the active element actuator 236. Most any RF active element may be used within the electrosurgical device 500. For simplicity's sake, however, the stem and bulb active element 218 of FIGS. 16–18 is again used here, it being understood that this embodiment is not limited thereby. As shown in FIGS. 19–20, the distal end 208 of the probe body 202 may be shaped as a non-coring needle. As shown in FIG. 19, the active element 218 may be recessed within the internal lumen 217 of the probe body to define an electrically insulating layer 219. The layer 219 may also physically isolate the active element 218 from the patient's tissue when the active element is in its non-deployed state, as shown in FIG. 19. When the device 500 is properly positioned within the patient (as verified, for example, through the use of ultrasound) and the active element 218 energized, the active element actuator 236 may be used to advance the energized active element 218 in the distal direction 296 until the active element 218 emerges from the distal opening 292 and extends to the desired length, as shown in FIG. 20. The insulating layer 219 (FIG. 19) between the active element 218 and the opening 294 defined in the distal end of the probe body 202 (and/or the tissue 214) prevents any of the RF current applied to the active element 218 from dissipating into the patient's tissue 214 during the energizing of the active element 218.

Some or all of the through holes 938 may be utilized for the delivery of a fluid to the patient during the procedure, such as antibiotic agents, analgesic agents or most any pharmaceutical agent. Such agents may be administered to the patient from the port 942. Alternatively, the port 942 may be coupled to suction and some or all of the through holes 938 may be utilized to suction out the operative site of smoke, blood or other bodily fluids during or after the operative procedure. Alternatively still, more than one port 942 may be provided in the proximal portion 902 and more than one internal lumen 940 may be defined along the length of the probe 500. The additional lumen may be in fluid communication with selected through holes 938. By this structure, both delivery of a pharmaceutical agent and suctioning may be provided within a single probe 500. It is to be understood that any of the devices according to the present invention may incorporate all or a portion of the structures referenced by 938, 940 and 942 or like structures to provide suctioning and/or fluid delivery functionality.

Figure 21:
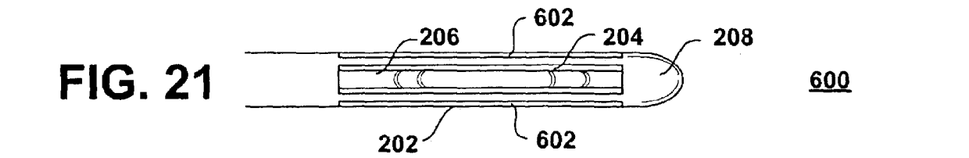
FIG. 21 is a top view of the distal end of an electrosurgical device according to a still further embodiment of the present invention.
Figure 22A:
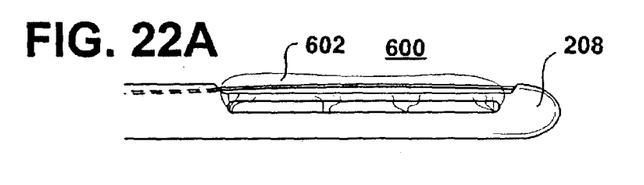
FIG. 22A is a side view of the device of FIG. 21, in which the inflatable balloon(s) thereof has (have) been inflated to create an insulating layer between the active element and the patient's tissue.
Figure 22B:
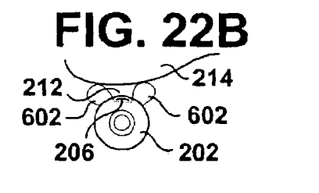
FIG. 22B is a front view of the device of FIG. 22A, in which the balloons are in their inflated configuration.
Figure 23:
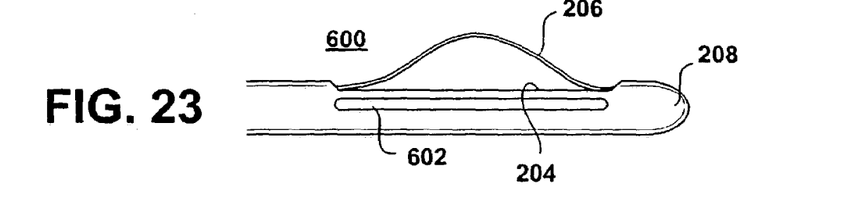
FIG. 23 is a side view of the device of FIG. 21, after deflation of the balloon(s) and deployment of the active element.

FIGS. 21–23 shows the distal portion of a still further embodiment of the present invention. As shown therein, the device 600 defines a distal end 208, a window 204 and an active element 206, as described above. The device 600 also includes one or more inflatable balloons 602. As best shown in FIG. 21, at least one such balloon 602 may advantageously be disposed in close proximity to and may be co-extensive with the window 204 from which the active element 206 emerges and deploys. FIG. 22A shows the device 600 in a configuration wherein the active element 206 is in its non-deployed configuration and the balloons 602 are in their inflated configuration. For example, the balloons 602 may be inflated with $CO_2$ (for example) from a $CO_2$ reservoir (not shown) located within or without the device 600. FIG. 22B shows a front view of the device of FIG. 22A and illustrates the insulating layer 212 between the active element 206 and the tissue 214 created by the inflation of the balloons 602. Finally, FIG. 23 shows a side view of the device 600 in a configuration wherein the active element 206 is deployed and the balloons 602 deflated, rendering them (preferably) flush or substantially flush with the outer surface of the device 600. In operation, the device 600 may be advanced through the patient's tissue 214 until the target area is reached. The balloon or balloons 602 may then be inflated, thereby creating the insulating layer 212 between the active element 206 and the tissue 214. The active element 206 may then be energized with RF current from a RF power supply, such as shown at 240 in FIG. 16, for example. After energizing the active element 206, the balloon 602 or balloons 602 may be deflated and the active element deployed, as described above. Once again, initially electrically insulating the active element 206 from the tissue 214 advantageously prevents current from dissipating into the tissue 214 during the energizing of the active element 206. Thereafter, the active element 206 may be brought into contact with the patient's tissue 214 when the active element 206 has been energized to a therapeutically effective level.

Figure 24:
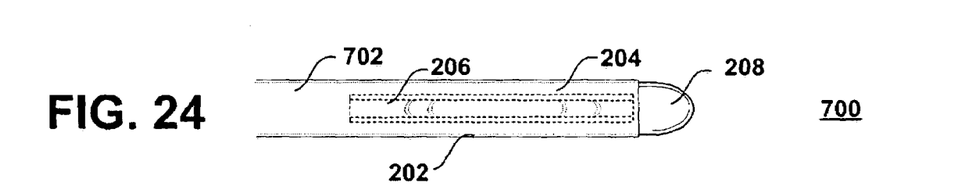
FIG. 24 shows a top view of the distal end of an electrosurgical device according to another embodiment of the present invention.
Figure 25:
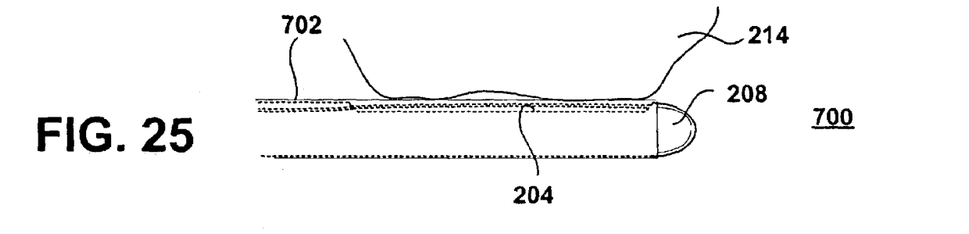
FIG. 25 shows a side view of the device of FIG. 24.
Figure 26:
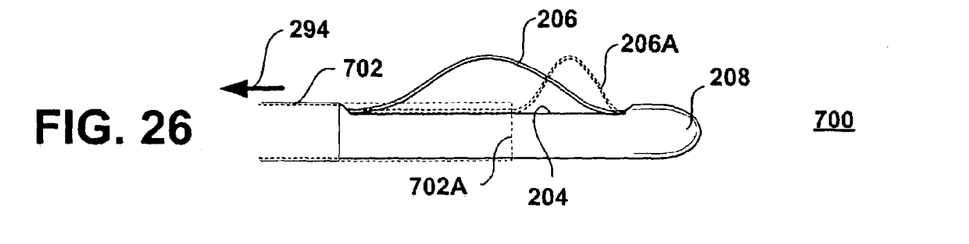
FIG. 26 shows the device of FIG. 25, after the outer sleeve thereof has been slid away from the window from which the active element is deployed.

FIGS. 24–26 show the distal portion of a still further embodiment of the present invention. As shown therein, the electrosurgical device 700 includes a probe body 202, a window 204 defined within the probe body 202 near the distal end 208 thereof, and an active element 206 within the window 204, as previously described. To electrically insulate the active element 206 during the energizing thereof using a RF power source (such as shown at 240 in FIG. 16), an electrically insulating outer sleeve 702 is fitted over the probe body 202. The outer sleeve 702 is configured to slide over and/or against the outer surface of the probe body 202 in the proximal and axial directions. Upon energizing the active element 206, the outer sleeve 702 may advantageously be maintained in a position wherein it prevents tissue 214 from coming into contact with the active element 206. After the active element 206 is energized, the physician may retract the outer sleeve 702 by sliding it in the proximal direction 294. By fully retracting the outer sleeve 702, the physician may expose the entire active element 206 to the tissue 214. However, by only partially retracting the outer sleeve 702, as shown at 702A, the physician may advantageously change the extent of deployment and/or shape of the active element, as shown at 206A.

It should also be noted that the active element in FIGS. 6–26 may also include a device to cause hypothermia and subsequent necrosis in the patient's tissue; i.e., to freeze the patient's tissue in contact with the active element. Indeed, by energizing such an active device while it is electrically insulated and/or physically isolated from the patient's tissue 214, the temperature of the active element will drop to the intended low temperature faster than if the active element were initially in contact with the patient's tissue 214, especially if the tissue is highly vascular (and thus able to transport heat efficiently).

Figure 27:
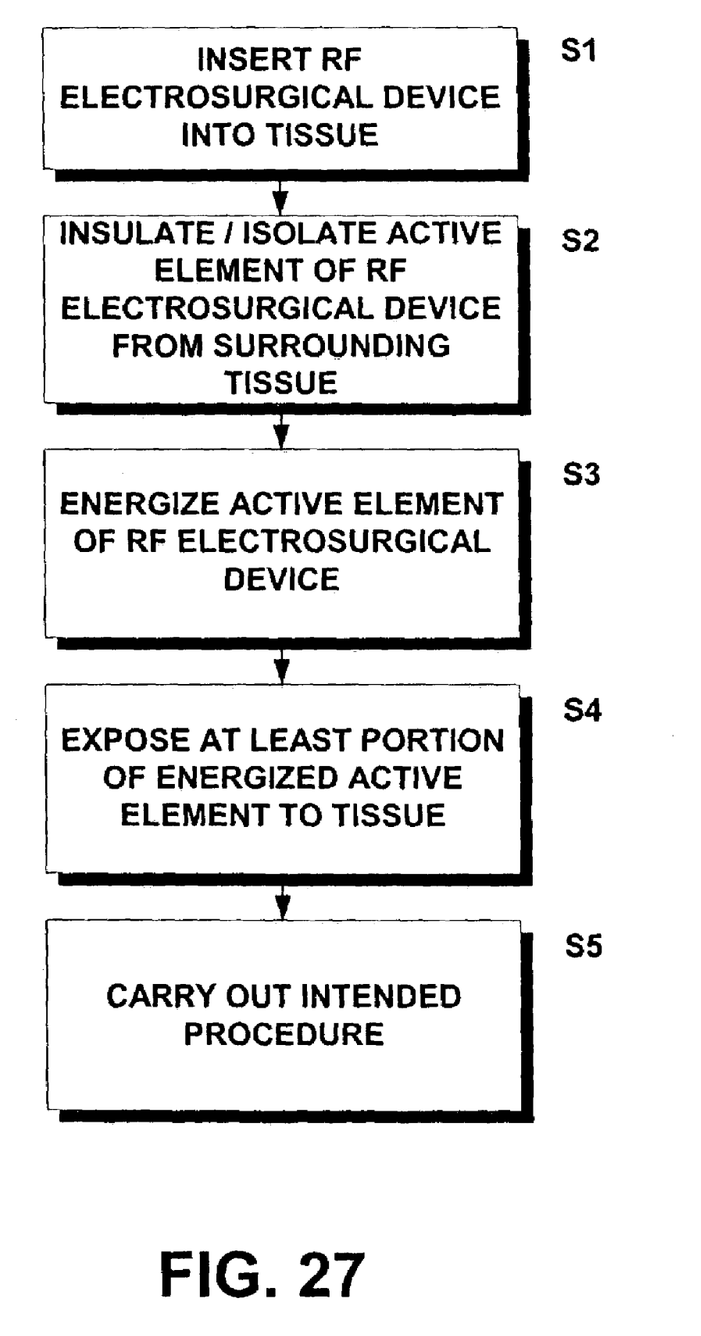
FIG. 27 is a flowchart of a method for carrying out an electrosurgical procedure according to an embodiment of the present invention.

FIG. 27 is a flowchart of a method of carrying out an electrosurgical procedure, according to the present invention. Step S1 calls for the insertion of a RF electrosurgical device, such as shown in FIGS. 6–26, into the patient's tissue. Advantageously, ultrasound (or any other radiological) guidance may be employed to guide the device to the targeted site within the patient's tissue. Step S2 calls for electrically insulating (and/or physically isolating) the active element (such as shown at 206, 218) of the RF device from the surrounding tissue. The insulating step S2 may be carried out either before, during or after step S1, but should be carried out before step S3—that is, before energizing the active element. Insulating and/or electrically isolating the active element may entail ensuring the presence of an insulating layer (preferably about 0.1 mm to about 5 mm in thickness) by maintaining the active element recessed within the probe body, in its retracted, non-deployed configuration and/or sliding a sliding door (216, 220) over the active element, inflating a balloon or balloons 602 and/or maintaining an outer sleeve 702 over the active element. Alternatively, any means of creating an insulating layer 212 and/or insulating the active element from the surrounding tissue during the energizing thereof may be employed within the scope of the present invention. Step S4 calls for exposing at least a portion of the energized active element to the patient's tissue and step S5 calls for carrying out the intended procedure, such as cutting, ablation, coagulation, etc.

Figures 28, 29:
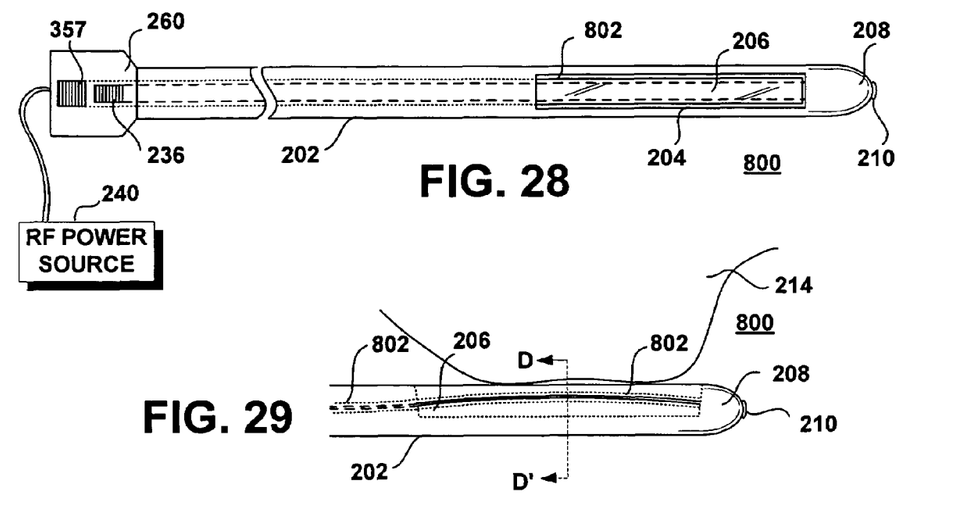
FIG. 28 is a top view of an electrosurgical device, according to another embodiment of the present invention.
FIG. 29 is a side view of the distal portion of the device of FIG. 28, showing the active element thereof in its non-extended and sheathed state.
Figure 30:
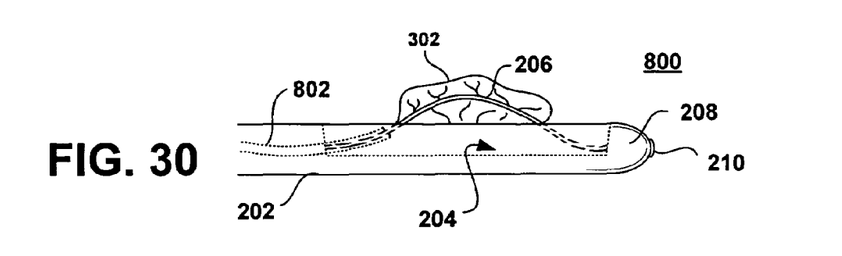
FIG. 30 is a side view of the distal portion of the device of claim 28, showing the active element thereof in its extended and unsheathed state.
Figure 31:
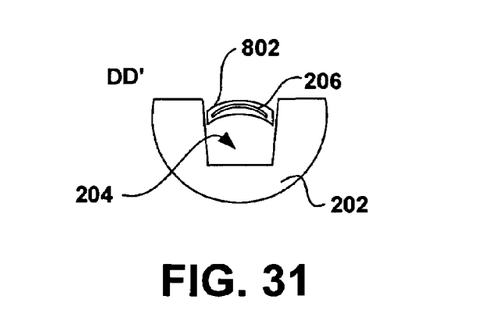
FIG. 31 is a cross-sectional view of the electrosurgical device of FIG. 29, taken along cross-sectional lines DD'.
Figure 32:
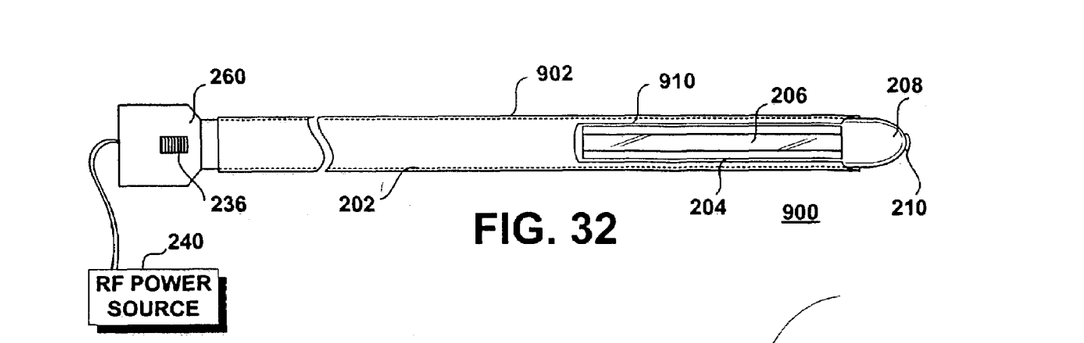
FIG. 32 is a top view of an electrosurgical device, according to another embodiment of the present invention.

FIGS. 28–31 represent different views of an electrosurgical device 800, according to another embodiment of the present invention. Considering now FIGS. 28–31 collectively, the device 800 includes a proximal end 260, a distal end 208 and may include a distal RF element 210, as described above. The device 800 includes an active element 206, which may include one or more wires and/or loops, or any other therapeutically effective RF element effective to cut, dissect, fulgurate, induce hyper or hypothermia (from a different power source) and/or to desiccate tissue using RF power. The active element 206 may be electrically coupled to a power source, such as the RF power source 240. The embodiment illustrated in FIGS. 28–31 is configured to selectively electrically insulate and/or physically isolate the active element 206 from the patient's tissue 214. Indeed, the active element 206 may be selectively insulated and/or isolated from the patient's tissue 214 by means of an insulating sleeve 802 that is configured to at least partially surround and at least partially cover the active element 206, as most clearly shown in the cross-sectional view of FIG. 31. The insulating sleeve 802 is further configured to slide over the active element 206 and to loosely cover the element 206, as shown in FIG. 29. When the active element 206 is fully energized, the sleeve 802 may be retracted in the proximal direction (toward the physician) using an appropriate actuator such as the insulating sleeve actuator 357 for example, thereby exposing the active element 206 to the patient's tissue and enabling deployment of the active element 206, as shown in FIG. 30. The active element may include one of a ribbon and wire, said one of ribbon and wire being adapted to selectively bow out of the window when transitioning from the non-deployed configuration to the deployed configuration. A tissue collection means may be attached thereto or trail behind the active element, as disclosed in co-pending and commonly assigned U.S. patent application Ser. No. 09/565,611 filed on May 4, 2000 and/or commonly assigned U.S. Pat. No. 6,022,362 filed on Sep. 3, 1998, the disclosure of each being incorporated herein by reference in its entirety. The insulating and retractable sleeve 802 may include or be formed of a flexible material, such as a silicone elastomer (such as polydimethyl siloxane, for example). During the procedure, the active element 206 may be retracted within the window 204 defined within the probe body and the insulating sleeve 802 advanced in the distal direction (i.e., toward the distal end 208). This may enable the operator to remove any char that may have adhered to the active element 206 without, however, removing the probe 800 from the patient.

Figure 33:
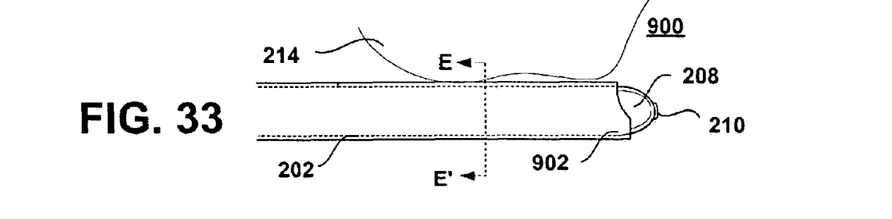
FIG. 33 is a side view of the distal portion of the device of FIG. 32.
Figure 34:
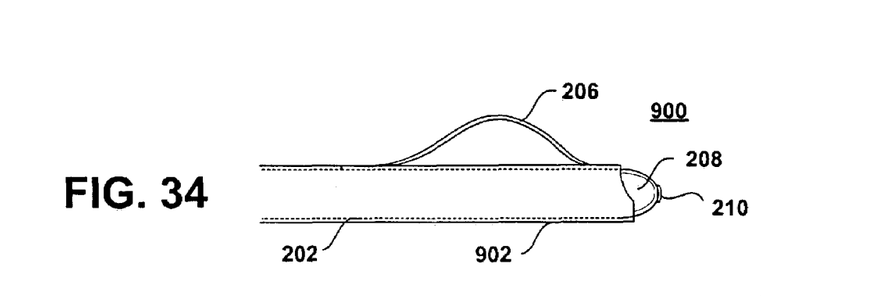
FIG. 34 is a side view of the distal portion of the device of FIG. 32, in which the active element is in its extended state.
Figure 35:
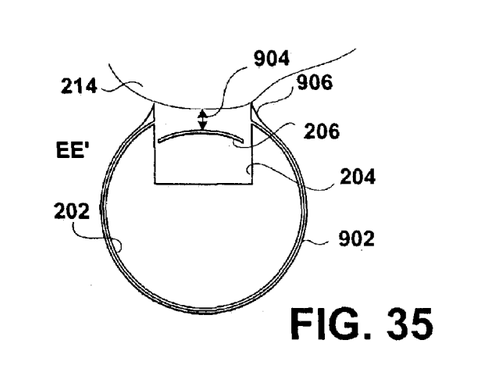
FIG. 35 is a cross-sectional view of the electrosurgical device of FIG. 33, taken along cross-sectional lines EE'.
Figure 36:
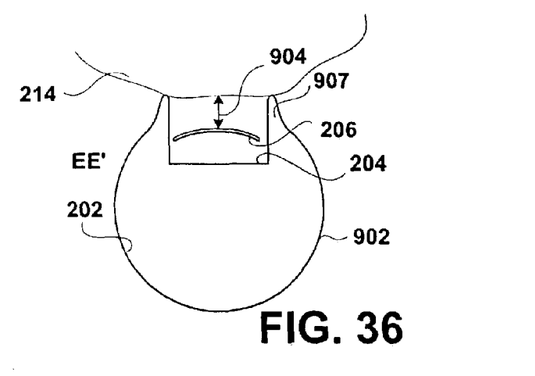
FIG. 36 shows a cross-sectional view of another embodiment of the electrosurgical device of FIG. 33, taken along cross sectional lines EE'

FIGS. 32–36 show a still further embodiment of the present invention, in which the active element 206 of the electrosurgical device 900 is initially electrically insulated from the patient's tissue 214 not by an insulating sleeve, but by an external sheath 902 (FIGS. 32–35) or by the configuration or topology of the probe body 200 (FIG. 36). Considering FIGS. 32–35 collectively, this embodiment of the electrosurgical device 900 of the present invention includes a probe body 202 defining a proximal end 260 and a distal end 208. The device 900 includes an active element 206, which may include one or more wires and/or loops, or any other therapeutically effective element effective to cut, dissect, fulgurate, or induce hyper or hypothermia. The active element 206 may be electrically coupled to a power source, such as the RF power source 240. The device 900 may also include a distal RF element 210. As shown, the device 900 may also include an insulating sheath 902 disposed over at least a portion of the probe body 202. According to the present invention, the sheath 902 may include a cutaway portion 910 that may be aligned with and expose the underlying window 204 defined within the probe body 202. As shown in FIG. 33, when the active element 206 is in its retracted position, the insulating sheath 902 electrically insulates the active element 206 from the patient's tissue 214, whereas the sheath 902 does not interfere with the active element 206 when the active element 206 is in its extended configuration, as shown in FIG. 34. Suction may be advantageously employed here to clear the operative site from electrically conductive bodily fluids and/or smoke. As shown most clearly in the cross-sectional view of FIG. 35, the sheath 902 may have a generally circular cross section, and may include one or more raised portions 906 adjacent to the window 204 and substantially aligned therewith. The raised portion(s) 906 enable the active element 206, in its retracted position, to be electrically insulated from the patient's tissue 214 by an insulating layer 904 measuring about 0.1 mm to about 5 mm in thickness, for example. In this manner, the active element 206 may be fully energized by the RF power source 240 before being brought into contact with the patient's tissue, with the accompanying advantages discussed above. The sheath 902 may cover all or only a portion of the probe body 202.

FIG. 36 shows another embodiment of the present invention, wherein the probe body alone is shaped so as to insulate the active element 206 from the patient's tissue 214 until the active element 206 is fully energized. As shown therein, the probe body 202 may include one or more locally raised portions 907 adjacent to the window 204 from which the active element 206 extends. The raised portion(s) 907 (raised about 0.5 mm to about 5 mm away from the outer surface of the probe body, for example) may be defined along the long sides of the window 204 or around the entire perimeter thereof. The raised portion(s) 907 need not be continuous, as long as they serve to effectively electrically insulate the tissue 214 from the active element 206 until the active element 206 is fully energized. As shown in FIG. 36, the tissue 214 is separated from the non-extended active element 206 by the insulating (air) layer 904 by the raised portions 907 of the probe body 202 which prevent the tissue 214 from prolapsing into the window 204 and coming into contact with the active element 206 until the physician chooses to extend the active element 206 and begin cutting the patient's tissue 214.

Any geometry of the sheath 902 and/or probe body 202 and/or active element that forms an insulating layer between the active element and the patient's tissue when the active element is in its non-deployed state falls into the scope of the present invention. Likewise, any structure that prevents the tissue 214 from prolapsing into the window 204 or that generally prevents the active element 206 from coming into contact with the tissue until the active element 206 is fully energized also falls within the scope of the present invention.

Figure 37:
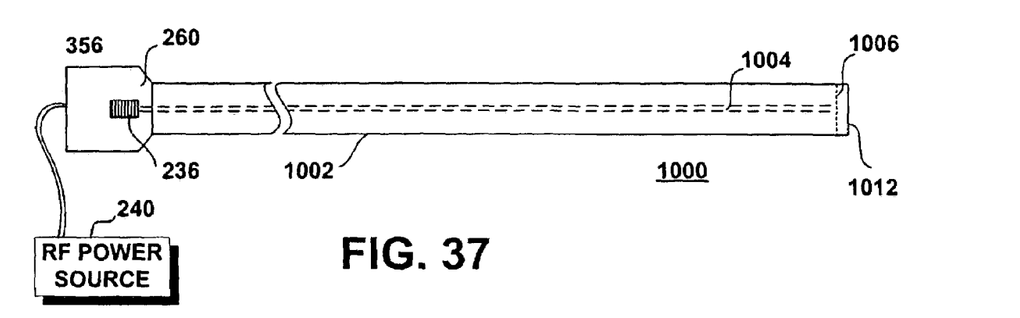
FIG. 37 shows another electrosurgical device, according to yet another embodiment of the present invention.
Figure 38:
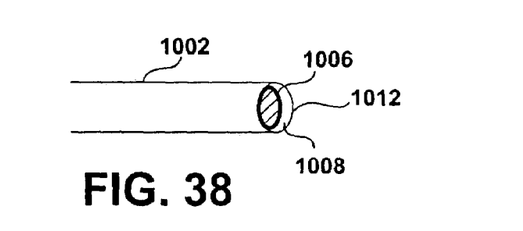
FIG. 38 is a perspective side view of the distal portion of the electrosurgical device of FIG. 37, in which the electrosurgical ring is in its non-extended state.
Figure 39:
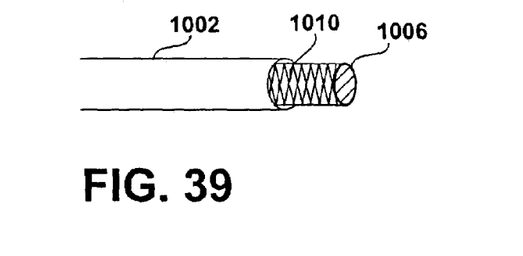
FIG. 39 is a perspective side view of the distal portion of the electrosurgical device of FIG. 37, in which the electrosurgical ring is in its extended state.

The present invention, moreover, is not limited to any particular active element. Indeed, although the embodiments of the present invention are herein illustrated with an extendible loop active element, the present invention is not so limited. An important aspect of the present invention is the electrical insulation and/or physical isolation of the active element of an electrosurgical device from the patient's tissue until the active element is fully energized. This aspect is again illustrated in FIGS. 37–39, in which the active element is shown as having a ring shape and the probe body little more than a hollow cannula. The electrosurgical device 1000 shown in FIGS. 37–39 includes a probe body 1002 that defines a proximal end 260 and a distal end 1012. An active element actuator 236 is configured to extend and retract a ring-shaped RF element 1006 from and back into the distal end 1012 of the probe body 1002. The ring-shaped active element 1006 is electrically coupled to the RF power source 240 and mechanically coupled to the actuator 236 by means of rod 1004 or by other means known to those of skill in this art. FIG. 38 shows the distal end 1012 of the probe body 1002 and the ring-shaped active element 1006 in its retracted position. In accordance with the present invention, the active element 1006 is electrically insulated from the patient's tissue (not shown) by virtue of its recessed position (recessed by a distance of about 0.1 mm to about 5 mm, for example) within the probe body 1002. Suction may be employed to maintain the recess clear of bodily fluids. This enables the physician to insure that the active element 1006 is fully energized before the active element 1006 is deployed or extended (see FIG. 39) out of the distal end 1012 of the probe body 1002 and comes into contact with the patient's tissue. As shown in FIG. 39, a mesh or other membrane 1010 may be attached to and trail the active element 1006 to collect tissue cut by the active RF element 1006. This mesh may be expandable, to enable the collection of a relatively large mass of tissue. Likewise, the ring-shaped active element 1006 may itself be expandable in diameter or deformed in shape so as to enable collection of large or irregularly shaped lesions or specimens.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. An electrosurgical device, comprising:
  a body having an outer surface, a proximal end, and a distal end;
  an elongate active element having a distal end coupled to the distal end of the body, the active element being adapted to be electrically connected to a power source and configured to selectively assume a non-deployed configuration and a deployed configuration, the elongate active element being in a straightened configuration in the non-deployed configuration and being in a bowed condition in which the active element extends radially away from the outer surface of the body when in the deployed configuration;

a tissue collection element that is configured to substantially span a length of the elongate active element coming into contact with tissue, the tissue collection element being configured to radially trail behind the active element and to collect tissue cut by the active element when the active element is in the deployed configuration and rotated, and an insulating sleeve, the insulating sleeve being slidable relative to the active element to cover at least part of the active element from a patient's tissue in a first position and expose the active element to the patient's tissue in a second position.

2. The device of claim 1, wherein the active element includes one of a ribbon and wire, said one of ribbon and wire being adapted to selectively bow out of a window when transitioning from the non-deployed configuration to the deployed configuration.

3. The device of claim 1, wherein the active element is configured to carry out at least one of tissue ablation, dissection, fulguration, cautery, desiccation, hyperthermia and hypothermia.

4. The device of claim 1, wherein the power source includes an RF power source.

5. The device of claim 1, wherein a window is disposed one of near the distal end of the body and at the distal end thereof.

6. The device of claim 1, further including suction means for controllably removing fluids from an excision site in the patient's tissue.

7. A method of treating tissue using a probe, comprising the steps of:

providing a elongate probe having an active element electrically connected to a power source, the active element being movable between a non-deployed configuration to a deployed configuration that extends radially away from an outer surface of the probe, the deployed configuration being a bowed shape, the probe including a tissue collection element that is configured to substantially span a length of the elongate active element coming into contact with tissue, the tissue collection element being configured to radially trail behind the active element and to collect tissue cut by the active element when the active element is in the deployed configuration and rotated, the probe further including a movable insulating sleeve that is slidable relative to the active element between a first position and a second position, at least part of the active element being covered by the sleeve in the first position and being exposed in the second position;

inserting the probe into the tissue;

energizing the active element using power from the power source;

rotating the probe so that the active element sweeps though the tissue while in the deployed configuration and while energized such that the tissue collection element collects the tissue cut by the active element, the sleeve being in the second position during rotation of the probe.

8. The method of claim 7, wherein the power source is adapted to supply RF power to the active element.

9. The method of claim 7 wherein:

the providing step is carried out with only one active element.

* * * * *